(12) United States Patent
Courage

(10) Patent No.: US 9,364,214 B2
(45) Date of Patent: Jun. 14, 2016

(54) CANNULATED INSTRUMENT WITH CURVED SHAFT FOR PASSING SUTURE THROUGH TISSUE

(75) Inventor: Olivier Courage, Le Havre (FR)

(73) Assignee: Arthrex, Inc., Naples, FL (US)

( * ) Notice: Subject to any disclaimer, the term of this patent is extended or adjusted under 35 U.S.C. 154(b) by 2269 days.

(21) Appl. No.: 10/886,539

(22) Filed: Jul. 9, 2004

(65) Prior Publication Data

US 2005/0033365 A1 Feb. 10, 2005

Related U.S. Application Data

(60) Provisional application No. 60/485,740, filed on Jul. 10, 2003.

(51) Int. Cl.
*A61B 17/06* (2006.01)
*A61B 17/04* (2006.01)
*A61B 17/00* (2006.01)

(52) U.S. Cl.
CPC ....... *A61B 17/06109* (2013.01); *A61B 17/0485* (2013.01); *A61B 2017/00867* (2013.01); *A61B 2017/061* (2013.01); *A61B 2017/0608* (2013.01)

(58) Field of Classification Search
CPC ........... A61B 17/0469; A61B 17/0485; A61B 17/0483; A61B 17/06109; A61B 17/0482; A61B 2017/0498; A61B 2017/06076; A61B 2017/0608; A61B 2017/061

USPC .......................................... 606/139, 144, 148
See application file for complete search history.

(56) References Cited

U.S. PATENT DOCUMENTS

| | | | | |
|---|---|---|---|---|
| 3,877,434 A * | 4/1975 | Ferguson et al. | ............ | 606/158 |
| 5,250,055 A * | 10/1993 | Moore et al. | .................. | 606/148 |
| 5,312,423 A * | 5/1994 | Rosenbluth et al. | .......... | 606/148 |
| 5,499,991 A * | 3/1996 | Garman et al. | ............... | 606/148 |
| 5,501,692 A * | 3/1996 | Riza | .............................. | 606/148 |
| 5,562,683 A * | 10/1996 | Chan | ............................ | 606/139 |
| 5,637,112 A * | 6/1997 | Moore et al. | .................. | 606/148 |
| 5,643,292 A * | 7/1997 | Hart | .............................. | 606/144 |
| 5,653,716 A * | 8/1997 | Malo et al. | .................... | 606/139 |
| 5,681,333 A * | 10/1997 | Burkhart et al. | .............. | 606/148 |
| 5,904,692 A * | 5/1999 | Steckel et al. | ................ | 606/139 |
| 6,074,403 A | 6/2000 | Nord | | |
| 6,245,081 B1 * | 6/2001 | Bowman et al. | ............. | 606/148 |
| 6,517,564 B1 | 2/2003 | Grafton et al. | | |
| 6,620,166 B1 * | 9/2003 | Wenstrom et al. | .............. | 606/72 |
| 6,629,984 B1 * | 10/2003 | Chan | ............................ | 606/148 |

* cited by examiner

*Primary Examiner* — Alexander Orkin
(74) *Attorney, Agent, or Firm* — Blank Rome LLP

(57) ABSTRACT

A surgical instrument for manipulating suture within a patient. The surgical instrument includes a short cannulated handle and a cannulated shaft having a curved configuration. A Nitinol loop is inserted through the cannulation of the instrument for passing and shuttling suture through tissue. The curved shaped of the instrument allows it to be introduced into the shoulder for rotator cuff repair, for example, using the Neviaser Portal.

6 Claims, 4 Drawing Sheets

CANNULATED INSTRUMENT WITH CURVED SHAFT FOR PASSING SUTURE THROUGH TISSUE

This application claims the benefit of U.S. Provisional Application No. 60/485,740, filed Jul. 10, 2003, the entire disclosure of which is incorporated by reference herein.

FIELD OF THE INVENTION

The present invention relates to arthroscopic surgical methods and instruments and, more specifically, to a method and instrument for passing suture through the rotator cuff via the Neviaser Portal.

BACKGROUND OF THE INVENTION

Arthroscopic suturing techniques and instruments have been developed to facilitate the suturing of tissue during arthroscopic surgical procedures. In arthroscopic surgery, access to a surgical work site within a patient's body is normally provided through one or more portals formed directly in the patient's body, or through one or more cannulas inserted into the patient's body through small incisions. A chosen surgical procedure is carried out by a surgeon through the use of elongated instruments inserted through these cannulas and it often becomes necessary to suture selected tissue at the surgical work site.

Since the work site is only accessible through a small portal or cannula, and since it is very difficult to tie sutures within the body, various devices and techniques have been developed to enable the surgeon to tie sutures arthroscopically. For example, some procedures enable the surgeon to pass suture material through selected tissue, form a surgical knot extracorporeally and then move the knot with a knot pusher through the portal or cannula into position adjacent the desired tissue to be sutured. Other instruments, such as the suture retriever instruments disclosed and claimed in U.S. Pat. Nos. 6,074,403 and 6,517,564, include a shaft terminating in a sharp tip for piecing tissue and a hinged jaw for capturing and retrieving suture. Still other instruments for passing suture, such as the Suture Lasso, sold by Arthrex, Inc. of Naples, Fla., incorporate a hollow needle for piercing tissue, and a wire loop insertable through the needle for retrieving suture.

Arthroscopic rotator cuff repair is sometimes performed through a superior, percutaneous portal called the Modified Neviaser Portal. As shown in FIG. 1, the Modified Neviaser Portal 50 is located about 1 centimeter posterior to acromioclavicular joint 52 of shoulder 54, midway between the clavicle and spine of the scapula. Due the position of the patient's neck in the Beach Position, it is extremely difficult to pass an instrument, such as those described above, into the shoulder 54 via the Modified Neviaser Portal 50. Accordingly, it would be desirable to provide an instrument and method for rotator cuff repair which can be passed through the Neviaser Portal with the patient in the Beach Position.

SUMMARY OF THE INVENTION

The present invention provides a surgical instrument for retrieving suture within a patient. The surgical instrument includes a short handle and a cannulated shaft having a curved configuration. The curved cannulated shaft receives a wire loop that allows suture to pass through tissue. The curved shaped of the instrument and the shortened handle allows it to be introduced, for example, into the shoulder for rotator cuff repair using the Modified Neviaser Portal.

These and other features and advantages of the invention will become apparent from the following detailed description that is provided in connection with the accompanying drawings and illustrated exemplary embodiments of the invention.

DETAILED DESCRIPTION OF THE PREFERRED EMBODIMENTS

Figure 1:
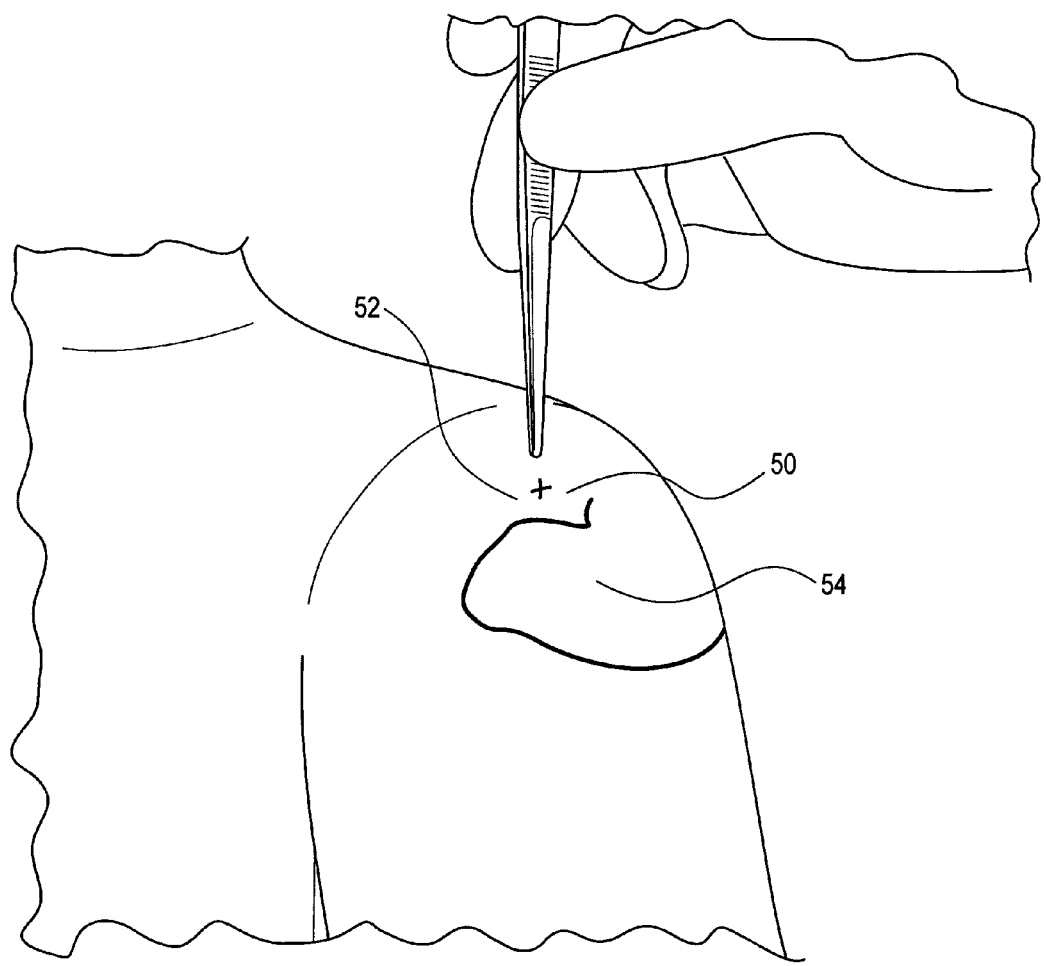
FIG. 1 illustrates a partial top view of a shoulder of a patient positioned in the Beach Position, indicating the location of the Neviaser Portal on the patient's shoulder.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The term "endoscopy" encompasses arthroscopy, laparoscopy, hysteroscopy, among others, and endoscopic surgery involves the performance of surgical procedures within a patient's body through small openings as opposed to conventional open surgery through large incisions.

Referring now to the drawings, where like elements are designated by like reference numerals, FIGS. 2-5 illustrate a surgical instrument 100 of the present invention for retrieving suture within a patient. As detailed below, the surgical instrument includes a short handle and a shaft having a curved configuration. The curved shaft receives a wire loop, for example a Nitinol loop, that is used to capture and pass suture through tissue. The curved surgical instrument 100 of FIGS. 2-5 may be employed, for example, to manipulate and retrieve suture during arthroscopic surgery. In particular, the curved shaped of the instrument allows it to be introduced into the shoulder for rotator cuff repair, percutaneously and medial to lateral, using the Modified Neviaser Portal.

The surgical instrument 100 preferably comprises an elongate, narrow diameter body or shaft assembly 10 suitable for use in remote procedures performed through percutaneous tissue punctures, such as vascular closures, arthroscopic, laparoscopic and other invasive procedures and the like. The shaft assembly typically has a length of about 5 cm to about 20 cm, preferably about 15 cm. The diameter of the shaft assembly is sufficiently small to facilitate introduction through access sheaths, cannulas, trocars, and the like, typically being less than about 10 mm, preferably about 5 to about 7 mm.

Figure 2:
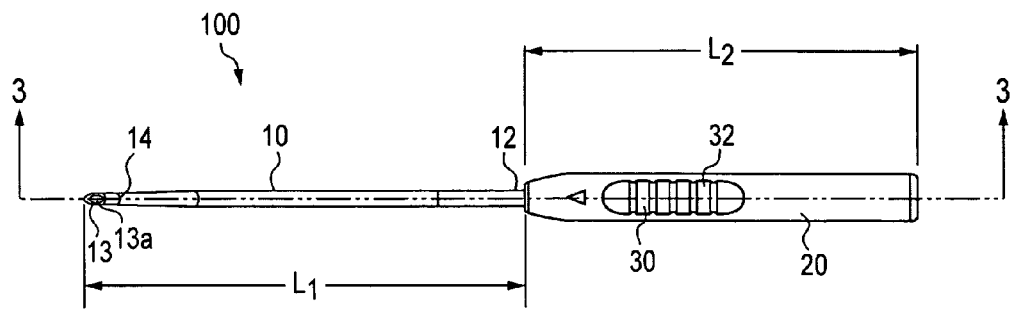
FIG. 2 illustrates a top view of a curved surgical instrument according to the present invention.
Figure 3:
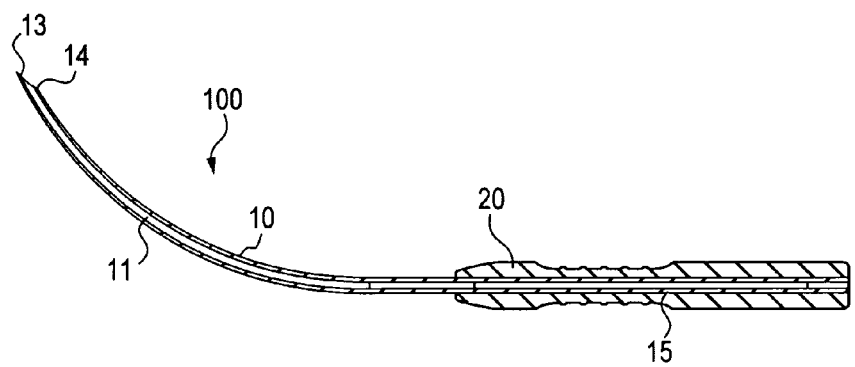
FIG. 3 illustrates a cross-sectional view of the curved surgical instrument of FIG. 2 taken along line A-A.

As illustrated in FIGS. 2-5, the shaft assembly 10 is elongated and cannulated and has a curved configuration. The shaft assembly 10 is provided with a substantially straight or linear region 15, which is adjacent to a substantially curved or bent region 11. The substantially curved or bent region 11 has a proximal end 12 and a distal end 14. A handle assembly 20 is provided at the proximal end 12 and houses the straight or linear region 15, as shown in FIGS. 2 and 3. The handle assembly 20 is provided with at least one recessed grip area 30 (FIGS. 2, 3 and 5) having protuberances 32 of various configurations and sizes, to allow easy manipulation by a surgeon. The outer diameter of the shaft assembly 10 is smaller than the inner diameter of the handle 20 and is securely fixed within the handle 20. As described in more detail below, the distal end 14 of the shaft is configured to engage and retrieve a suture, while the proximal end 12 of the shaft has the handle assembly designed to facilitate manual manipulation of the device.

The shaft or body assembly 10 of the surgical instrument 100 may have a round or oval cross-sectional shape. The curved region 11 of the shaft or body assembly 10 is formed of a rigid, medically acceptable metal or plastic material, preferably stainless steel. The linear region 15 of the body assembly 10 is formed of stainless steel or diamond knurl, and is surrounded by the handle assembly 20.

Figure 4:
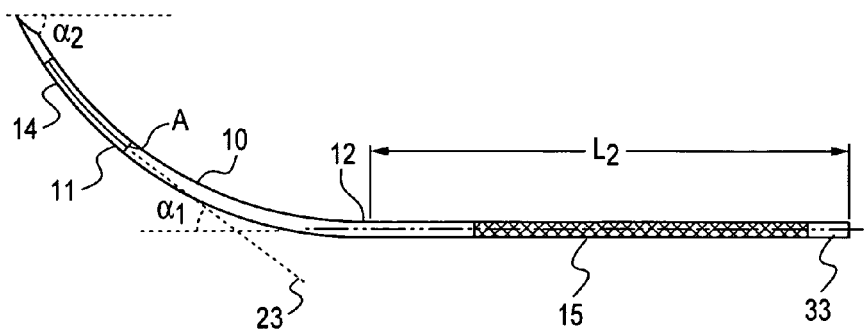
FIG. 4 illustrates a lateral view of the shaft of the curved surgical instrument of FIG. 2 without the handle.

As shown in FIG. 4, longitudinal axis 33 of the handle assembly 20 forms an angle $\alpha_1$ with the tangential 23 to the mid-point A of the curved region 11 of the shaft or body assembly 10. Angle $\alpha_1$ may be about 10° to about 90°, more preferably about 30°, depending on the configuration of the surgical site and/or the surgical procedure to be undertaken. Preferably, the curved region 11 of the shaft or body assembly 10 is substantially curved, in that about 80 to 100%, more preferably of about 90%, of its length is curved relative to the longitudinal axis 33 of the handle assembly 20. The substantially curved region 11 of the shaft or body assembly 10 has a length $L_1$ (FIG. 2) of about 5 cm to about 15 cm, preferably about 10 cm. Preferably, the length $L_1$ the substantially curved region 11 is about equal to length $L_2$ (FIG. 2) of the substantially linear region 15.

Figure 5:
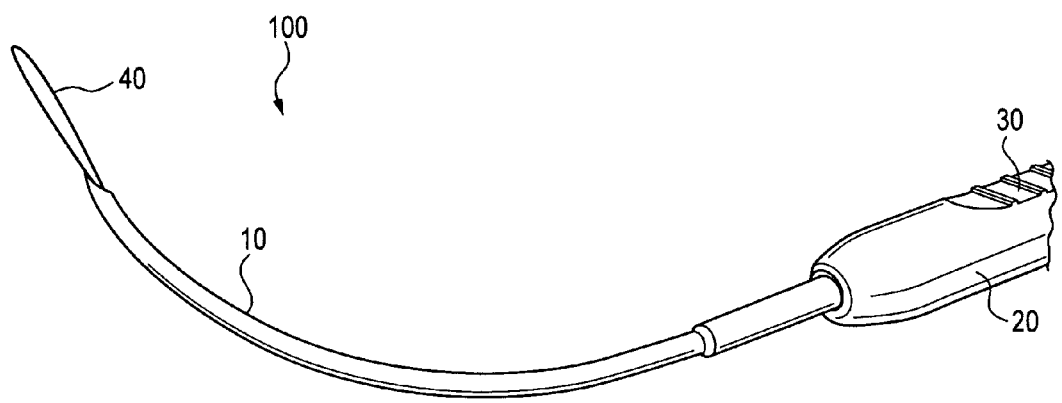
FIG. 5 illustrates a perspective view of the curved surgical instrument of FIG. 2 provided with a wire loop.

As illustrated in FIGS. 2 and 3, the distal end 14 of the substantially curved region 11 is provided with a sharp needle tip 13 having opening 13a (FIG. 1) that allows a wire loop 40 (FIG. 5), preferably a braided Nitinol loop 40, to be pushed through the surgical instrument 100 and to extend out the sharp needle tip 13 of the instrument, as shown in FIG. 5. Since the braided Nitinol loop 40 must pass through the instrument 100 without any interference, the edges of the opening 13a must not abrade the Nitinol loop 40 or the suture to be subsequently retrieved. Accordingly, the edges of the opening 13a are preferably beveled and form an angle $\alpha_2$ (FIG. 4) of about 45° with the longitudinal axis 33 of the instrument.

The surgical instrument 100 of the present invention described above with reference to FIGS. 2-5 may be employed in various surgical medical procedures for retrieving, transferring, treating, closing and/or tightening sutures and suture loops during surgical procedures. For example, the suture retrieving instrument 100 may be employed in endoscopic and arthroscopic procedures, including but not limited to arthroscopic rotator cuff repair, Bankhart shoulder repair, meniscal repair, and any orthopaedic procedure that requires manipulation of suture through soft tissue or bone tunnels, for example, or in conjunction with fixation devices, such as suture anchors. Additionally, the instrument 100 may be utilized in other general surgical and specialty procedures that require suturing at a remote site, such as inside the body. The instrument of the present invention may be also used in repairs where suture visibility or finger access can be limited. As a result of its curved configuration, the suture retriever instrument 100 of the invention has particular applicability to rotator cuff repair procedures, during which the instrument can be easily passed through the Neviaser Portal while the patient is positioned in the Beach Position.

It will be appreciated, of course, that while the surgical instrument 100 may be particularly useful for performing remote procedures through access sheaths, cannulas and trocars, it will also find use in open surgical procedures where its ability to capture suture will also provide advantages.

The surgical instrument 100 of the present invention may also be used without the Nitinol loop 40, as a suture passing instrument. For example, a stiff suture such as FiberStick sold by the assignee of the present application, Arthrex, Inc., may be inserted through the cannulated shaft 10 of the surgical instrument 100 and after piercing of the tissue with sharp needle tip 13 of the instrument. The end of the FiberStick suture that has been passed through the tissue may then be retrieved and used to tie down the tissue.

Figure 6:
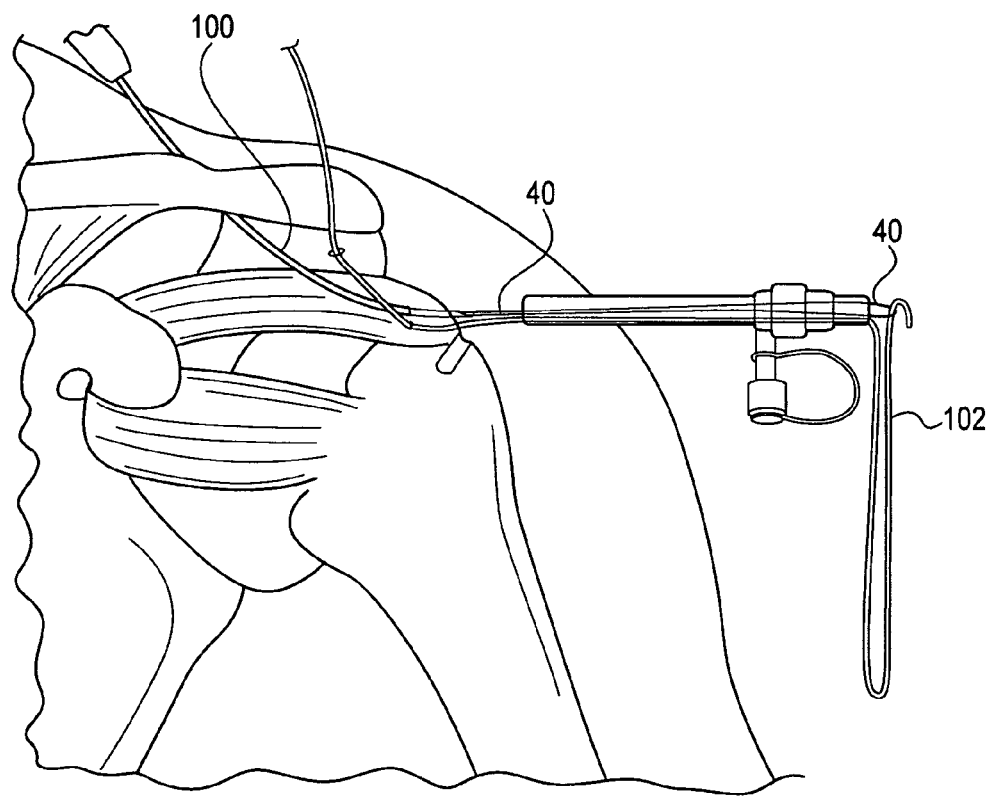
FIG. 6 is a view of a suture retrieving operation according to a method of the present invention.

To better illustrate an exemplary surgical procedure conducted with the suture retrieving instrument 100 of the present invention, reference is now made to FIG. 6, which illustrates a method of rotator cuff repair in which instrument 100 is inserted percutaneously through the rotator cuff, medially to laterally, through the Modified Neviaser Portal. The Nitinol loop 40 is retrieved out of a lateral cannula. A limb or end of suture 102 (such as #2 TigerWire suture sold by the assignee of the present application, Arthrex, Inc.) is shuttled through the cuff 104 and retrieved out an anterior accessory portal without removing instrument 100 from the subcromial space. Instrument 100 is then reinserted, through the rotator cuff, parallel to the first stitch. The Nitinol loop 40 is then retrieved out of the lateral cannula, the opposite end of the suture is placed in the loop and instrument 100 is removed, creating a mattress stitch. The second suture end is then retrieved out of the anterior accessory portal. With the rotator cuff now securely attached to suture, the cuff can be now be secured to the acromion, via the attached suture, using a tenodesis screw.

In an alternative technique of using the instrument of the present invention, a suture anchor is appropriately placed, in the desired location; a limb of suture from the suture anchor is retrieved out through a working cannula. The instrument 100 is instroduced percutaneously, aiming medial to lateral utilizing the Modified Neviaser Portal. Once the instrument is visualized in the subacromial space, it is passed through the rotator cuff tissue. The braided Nitinol loop is deployed. The suture limb is passed through the Nitinol loop. The instrument 100 is removed, passing suture through the rotator cuff. In some situations, it may also be desirable to remove the instrument 100, leaving the loop 40 and the captured suture 102 in place, and then subsequently manually withdraw the loop to retrieve the suture end 102.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed is:

1. A method of endoscopically retrieving suture disposed within a patient during an arthroscopic rotator cuff repair, comprising the steps of:

providing a fully cannulated suture retrieving instrument having a longitudinal axis, the suture retrieving instrument comprising: a cannulated shaft having a linear region and a curved region terminating in a sharp needle tip, wherein the length of the linear region is approximately equal to the length of the curved region; and a short handle coupled to an end of the cannulated shaft opposite the sharp tip, the handle being fully cannulated and being configured to house and surround the linear region completely, the linear region extending completely through the cannulation of the handle, wherein the curved region has a length of about 10 cm, wherein about 80 to about 100% of the length of the curved region is curved relative to the longitudinal axis, and wherein a longitudinal axis of the handle forms an angle of about 30 degrees with a tangential to a midpoint of the curved region;

positioning the suture retrieving instrument at a shoulder of the patient in the proximity of a rotator cuff to be sutured at a surgical site and during the arthroscopic rotator cuff repair;

advancing the suture retrieving instrument percutaneously through the shoulder, medially to laterally, via a Modified Neviaser Portal, to pierce the rotator cuff with the sharp needle tip, and passing the instrument through the rotator cuff, wherein the curved region of the cannulated shaft of the instrument allows it to be introduced into the shoulder using the Modified Neviaser Portal;

subsequently, inserting a loop through a proximal end of the cannulated handle and directly into the linear region of the shaft extending completely through the cannulation of the handle, and passing the loop through the entire length of the cannulated handle and the cannulated shaft so that the loop is pushed through entire suture retrieving instrument to extend out of an opening of the sharp needle tip;

subsequently, retrieving the loop out of a lateral cannula;

capturing suture disposed within the patient with the loop and shuttling one limb of the captured suture through the rotator cuff and retrieving the one limb out an anterior accessory portal to form a first stitch, without removing the suture retrieving instrument from subacromial space;

subsequently, reinserting the suture retrieving instrument through the rotator cuff and parallel to the first stitch;

retrieving the loop out of the lateral cannula and placing an opposite end of the suture in the loop; and removing the suture retrieving instrument to form a mattress stitch in the rotator cuff.

2. The method of claim 1, wherein the loop is a braided Nitinol loop.

3. The method of claim 1, wherein the suture is attached to a suture anchor.

4. The method of claim 1, wherein the captured suture is withdrawn from the surgical site by simultaneously withdrawing the instrument and the loop passing through the cannulation of the instrument.

5. The method of claim 1, wherein the captured suture is withdrawn from the surgical site by first withdrawing the instrument from the surgical site and subsequently withdrawing the loop with the captured suture from the surgical site.

6. The method of claim 1, wherein about 90% of the length of the curved region is curved relative to the longitudinal axis.

* * * * *